(12) United States Patent
Teisen et al.

(10) Patent No.: US 11,589,999 B2
(45) Date of Patent: Feb. 28, 2023

(54) ANGULATED RINGS AND BONDED FOILS FOR USE WITH BALLOONS FOR FUSION AND DYNAMIC STABILIZATION

(71) Applicant: DePuy Synthes Products, Inc., Raynham, MA (US)

(72) Inventors: Jacques Teisen, Zurich (CH); Joern Richter, Kandern (DE); Matthias Wesselmann, Ruedlingen (CH); Bodo Quint, Oberglatt (CH); Stefan Mueller, Buelach (CH)

(73) Assignee: DePuy Synthes Products, Inc., Raynham, MA (US)

( * ) Notice: Subject to any disclaimer, the term of this patent is extended or adjusted under 35 U.S.C. 154(b) by 149 days.

(21) Appl. No.: 17/060,072

(22) Filed: Sep. 30, 2020

(65) Prior Publication Data

US 2021/0015623 A1 Jan. 21, 2021

Related U.S. Application Data

(63) Continuation of application No. 16/165,692, filed on Oct. 19, 2018, now Pat. No. 10,828,170, which is a
(Continued)

(51) Int. Cl.
*A61F 2/44* (2006.01)
*A61B 17/70* (2006.01)
(Continued)

(52) U.S. Cl.
CPC .......... *A61F 2/441* (2013.01); *A61B 17/7097* (2013.01); *A61B 17/8855* (2013.01);
(Continued)

(58) Field of Classification Search
CPC ........ A61B 17/12022; A61B 17/12136; A61B 17/7097; A61B 17/8855; A61B 17/0057;
(Continued)

(56) References Cited

U.S. PATENT DOCUMENTS

| | | |
|---|---|---|
| 3,211,152 A | 10/1965 | Stern |
| 4,077,394 A | 3/1978 | McCurdy |

(Continued)

FOREIGN PATENT DOCUMENTS

| | | |
|---|---|---|
| DE | 10 2005 034 529 A1 | 1/2007 |
| EP | 1 913 903 A2 | 4/2008 |

(Continued)

OTHER PUBLICATIONS

Australian Office Action for Application No. 2014241511, dated Sep. 14, 2017 (5 pages).

(Continued)

*Primary Examiner* — Anu Ramana
(74) *Attorney, Agent, or Firm* — Barnes & Thornburg LLP (57) ABSTRACT

An inflatable and implantable balloon for treatment of degenerative disc disease, bones, lesions, spinal deformities and spinal motion segment instabilities. The balloon is comprised of adjustable and expandable volumes. Further disclosed are methods of forming, inserting, expanding, and implanting the multi-volume balloon for proper placement and stabilization of the spinal lesion or disease. Still further disclosed are kits for aligning and stabilizing elements of the spine.

4 Claims, 7 Drawing Sheets

Related U.S. Application Data continuation of application No. 15/408,148, filed on Jan. 17, 2017, now Pat. No. 10,143,561, which is a continuation of application No. 13/804,992, filed on Mar. 14, 2013, now Pat. No. 9,585,761.

(51) Int. Cl.
  *A61B 17/88* (2006.01)
  *A61F 2/46* (2006.01)
  *A61F 2/30* (2006.01)

(52) U.S. Cl.
  CPC ..... *A61F 2/4611* (2013.01); *A61F 2002/3008* (2013.01); *A61F 2002/30065* (2013.01); *A61F 2002/30451* (2013.01); *A61F 2002/30538* (2013.01); *A61F 2002/30545* (2013.01); *A61F 2002/30581* (2013.01); *A61F 2002/4677* (2013.01)

(58) Field of Classification Search
  CPC ............ A61B 2018/0025; A61F 2/441; A61M 25/1002; A61M 25/1011
  See application file for complete search history.

(56) References Cited

U.S. PATENT DOCUMENTS

| | | |
|---|---|---|
| 4,512,766 A | 4/1985 | Vailancourt |
| 4,856,510 A | 8/1989 | Kowalewski |
| 5,181,921 A | 1/1993 | Makita et al. |
| 5,306,310 A | 4/1994 | Siebels |
| 5,423,850 A | 6/1995 | Berger |
| 5,772,661 A | 6/1998 | Michelson |
| 5,827,289 A | 10/1998 | Reiley et al. |
| 6,066,154 A | 5/2000 | Reiley et al. |
| 6,127,597 A | 10/2000 | Beyar et al. |
| 6,228,022 B1 | 5/2001 | Friesem et al. |
| 6,468,200 B1 | 10/2002 | Fischi |
| 6,582,451 B1 | 6/2003 | Marucci et al. |
| 6,607,544 B1 | 8/2003 | Boucher et al. |
| 6,610,094 B2 | 8/2003 | Husson |
| 6,632,235 B2 | 10/2003 | Weikel et al. |
| 6,679,886 B2 | 1/2004 | Weikel et al. |
| 6,712,853 B2 | 3/2004 | Kuslich |
| 6,811,558 B2 | 11/2004 | Davison et al. |
| 7,056,345 B2 | 6/2006 | Kuslich |
| 7,074,226 B2 | 7/2006 | Roehm, III et al. |
| 7,108,705 B2 | 9/2006 | Davison et al. |
| 7,267,687 B2 | 9/2007 | McGuckin, Jr. |
| 7,300,456 B2 | 11/2007 | Andreas et al. |
| 7,503,920 B2 | 3/2009 | Siegal |
| 7,618,367 B2 | 11/2009 | Martin et al. |
| 7,618,431 B2 | 11/2009 | Roehm, III et al. |
| 7,643,884 B2 | 1/2010 | Pond, Jr. et al. |
| 7,666,205 B2 | 2/2010 | Weikel et al. |
| 7,666,226 B2 | 2/2010 | Schaller |
| 7,666,227 B2 | 2/2010 | Schaller |
| 7,670,374 B2 | 3/2010 | Schaller |
| 7,670,375 B2 | 3/2010 | Schaller |
| 7,717,956 B2 | 5/2010 | Lang |
| 7,740,659 B2 | 6/2010 | Zarda et al. |
| 7,785,368 B2 | 8/2010 | Schaller |
| 7,918,874 B2 | 4/2011 | Siegal |
| 7,947,078 B2 | 5/2011 | Siegal |
| 7,955,391 B2 | 6/2011 | Schaller |
| 7,955,931 B2 | 6/2011 | Appenzeller et al. |
| 7,959,684 B2 * | 6/2011 | Lin ............... A61B 17/8811 623/23.61 |
| 7,963,993 B2 | 6/2011 | Schaller |
| 7,967,864 B2 | 6/2011 | Schaller |
| 7,967,865 B2 | 6/2011 | Schaller |
| 3,007,535 A1 | 8/2011 | Hudgins et al. |
| 3,012,197 A1 | 9/2011 | Bashiri et al. |
| 8,057,544 B2 | 11/2011 | Schaller |
| 8,236,057 B2 | 8/2012 | Wirtel, III et al. |
| 8,460,383 B2 | 6/2013 | Wirtel, III et al. |
| 8,518,118 B2 | 8/2013 | Sack et al. |
| 9,358,120 B2 | 6/2016 | Richter et al. |
| 9,572,676 B2 | 2/2017 | Teisen et al. |
| 9,585,761 B2 | 3/2017 | Teisen et al. |
| 9,889,015 B2 | 2/2018 | Richter et al. |
| 10,143,561 B2 | 12/2018 | Teisen et al. |
| 10,828,170 B2 | 11/2020 | Teisen et al. |
| 10,864,085 B2 | 12/2020 | Richter et al. |
| 2002/0013601 A1 | 1/2002 | Nobles et al. |
| 2003/0018390 A1 | 1/2003 | Husson |
| 2003/0199979 A1 | 10/2003 | McGuckin |
| 2004/0230309 A1 | 11/2004 | DiMauro et al. |
| 2005/0070900 A1 | 3/2005 | Serhan et al. |
| 2005/0278027 A1 | 12/2005 | Hyde |
| 2007/0055265 A1 | 3/2007 | Schaller |
| 2007/0055275 A1 | 3/2007 | Schaller |
| 2007/0123986 A1 | 5/2007 | Schaller |
| 2007/0162136 A1 | 7/2007 | O'Neil et al. |
| 2007/0288095 A1 | 12/2007 | Wirtel et al. |
| 2008/0009943 A1 | 1/2008 | Zarda et al. |
| 2008/0133012 A1 | 6/2008 | McGuckin |
| 2008/0154272 A1 | 6/2008 | Schaller et al. |
| 2008/0234687 A1 | 9/2008 | Schaller et al. |
| 2008/0234827 A1 | 9/2008 | Schaller et al. |
| 2009/0088788 A1 | 4/2009 | Mouw |
| 2009/0118833 A1 | 5/2009 | Hudgins et al. |
| 2009/0182386 A1 | 7/2009 | Schaller |
| 2009/0222096 A1 | 9/2009 | Fried |
| 2009/0234454 A1 | 9/2009 | Siegal |
| 2009/0234457 A1 | 9/2009 | Lotz et al. |
| 2009/0248159 A1 | 10/2009 | Aflatoon |
| 2009/0275913 A1 | 11/2009 | Trieu |
| 2010/0076480 A1* | 3/2010 | Lu .................. G01F 11/022 366/139 |
| 2010/0198263 A1 | 8/2010 | Siegal et al. |
| 2010/0234954 A1 | 9/2010 | Justis et al. |
| 2010/0241177 A1 | 9/2010 | Schaller et al. |
| 2010/0249505 A1 | 9/2010 | Shoham et al. |
| 2010/0262147 A1 | 10/2010 | Siegal et al. |
| 2010/0262242 A1 | 10/2010 | Chavatte et al. |
| 2011/0004307 A1 | 1/2011 | Ahn et al. |
| 2011/0046737 A1 | 2/2011 | Teisen |
| 2011/0054408 A1 | 3/2011 | Wei et al. |
| 2011/0066192 A1 | 3/2011 | Frasier et al. |
| 2011/0092859 A1 | 4/2011 | Neubardt |
| 2011/0118789 A1 | 5/2011 | Siegal |
| 2011/0137332 A1 | 6/2011 | Sepetka et al. |
| 2011/0152683 A1 | 6/2011 | Gerrans et al. |
| 2011/0153019 A1 | 6/2011 | Siegal |
| 2011/0172710 A1 | 7/2011 | Thommen et al. |
| 2011/0178523 A1 | 7/2011 | Siegal et al. |
| 2011/0184515 A1 | 7/2011 | Siegal |
| 2011/0202133 A1 | 8/2011 | Siegal |
| 2011/0218494 A1 | 9/2011 | Gerrans et al. |
| 2011/0230967 A1 | 9/2011 | O'Halloran et al. |
| 2011/0245926 A1 | 10/2011 | Kitchen |
| 2011/0264146 A1 | 10/2011 | Siegal |
| 2011/0307063 A1 | 12/2011 | Schaller |
| 2011/0307064 A1 | 12/2011 | Schaller |
| 2012/0116399 A1 | 5/2012 | Appenzeller et al. |
| 2012/0191125 A1 | 7/2012 | Babkes et al. |
| 2012/0259215 A1 | 10/2012 | Gerrans et al. |
| 2012/0259216 A1 | 10/2012 | Gerrans et al. |
| 2014/0107789 A1 | 4/2014 | Schaller et al. |
| 2014/0277464 A1 | 9/2014 | Richter et al. |
| 2014/0277465 A1 | 9/2014 | Teisen et al. |
| 2014/0277466 A1 | 9/2014 | Teisen et al. |
| 2014/0277481 A1 | 9/2014 | Lee et al. |
| 2016/0250032 A1 | 9/2016 | Richter et al. |
| 2017/0119535 A1 | 5/2017 | Teisen et al. |
| 2018/0116813 A1 | 5/2018 | Richter et al. |
| 2019/0151107 A1 | 5/2019 | Teisen et al. |

FOREIGN PATENT DOCUMENTS

| | | |
|---|---|---|
| JP | 09-508292 A | 8/1997 |
| JP | 2006-517842 A | 8/2006 |
| JP | 2008-531140 A | 8/2008 |

(56) References Cited

FOREIGN PATENT DOCUMENTS

| | | |
|---|---|---|
| JP | 2009-504332 A | 2/2009 |
| JP | 2009-525827 A | 7/2009 |
| JP | 2009-537181 A | 10/2009 |
| JP | 2010-509985 A | 4/2010 |
| WO | 95/20362 A1 | 8/1995 |
| WO | 03/059213 A2 | 7/2003 |
| WO | 2004/073563 A2 | 9/2004 |
| WO | 2006/092015 A1 | 9/2006 |
| WO | 2007/022194 A2 | 2/2007 |
| WO | 2007/076049 A2 | 7/2007 |
| WO | 2007/095121 A2 | 8/2007 |
| WO | 2007/134374 A1 | 11/2007 |
| WO | 2008/063435 A1 | 5/2008 |
| WO | 2008/103781 A2 | 8/2008 |
| WO | 2008/103832 A2 | 8/2008 |
| WO | 2009/006432 A2 | 1/2009 |
| WO | 2013/023898 A1 | 2/2013 |

OTHER PUBLICATIONS

International Search Report for Application No. PCT/US2014/021236, dated Jun. 13, 2014 (7 Pages).
International Search Report for Application No. PCT/US2014/021248, dated Jun. 27, 2014 (7 Pages).
International Search Report for Application No. PCT/US2014/021266, dated Sep. 2, 2014 (9 Pages).
Japanese Office Action for Application No. 2016-500741, dated Feb. 6, 2018 (6 pages).
Japanese Office Action for Application No. 2016-500744, dated Aug. 28, 2018 (6 pages).
Japanese Office Action for Application No. 2016-500744, dated Dec. 5, 2017 (10 Pages).
Written Opinion for Application No. PCT/US2014/021266, dated Sep. 2, 2014 (10 Pages).
U.S. Appl. No. 13/804,336, filed Mar. 14, 2013, Expandable Coil Spinal Implant.
U.S. Appl. No. 13/804,992, filed Mar. 14, 2013, Angulated Rings and Bonded Foils for Use With Balloons for Fusion and Dynmaic Stabilization.
U.S. Appl. No. 13/827,060, filed Mar. 14, 2013, Adjustable Multi-Volume Balloon for Spinal Interventions.
U.S. Appl. No. 15/150,504, filed May 10, 2016, Expandable Coil Spinal Implant.
U.S. Appl. No. 15/408,148, filed Jan. 17, 2017, Angulated Rings and Bonded Foils for Use With Balloons for Fusion and Dynamic Stabilization.
U.S. Appl. No. 15/859,785, filed Jan. 2, 2018, Expandable Coil Spinal Implant.
U.S. Appl. No. 16/165,692, filed Oct. 19, 2018, Angulated Rings and Bonded Foils for Use With Balloons for Fusion and Dynamic Stabilization.

\* cited by examiner

ANGULATED RINGS AND BONDED FOILS FOR USE WITH BALLOONS FOR FUSION AND DYNAMIC STABILIZATION

CROSS-REFERENCE TO RELATED APPLICATIONS

This application is a continuation of U.S. patent application Ser. No. 16/165,692, filed on Oct. 19, 2018. U.S. patent application Ser. No. 16/165,692 is a continuation of U.S. patent application Ser. No. 15/408,148, filed on Jan. 17, 2017 (now U.S. Pat. No. 10,143,561). U.S. patent application Ser. No. 15/408,148 is a continuation of U.S. patent application Ser. No. 13/804,992, filed on Mar. 14, 2013 (now U.S. Pat. No. 9,585,761). The entire contents of these applications are incorporated by reference herein.

TECHNICAL FIELD

The technical field relates generally to inflatable and implantable balloons for treating degenerative disc disease, bone lesions, spinal deformities and spinal motion segment instabilities, and, more particularly, to adjustable balloons and methods of using the adjustable balloons within the intervertebral disc space, vertebral bodies, interspinous processes, or any spinal elements, to aim at restoring the original anatomy of the vertebral column.

BACKGROUND

Expandable medical devices, for example balloons, are commonly used for dilating and unblocking clogged or narrowed arteries (angioplasty). More recently, balloons have been used in surgical contexts other than angioplasty because the implants can be introduced into a surgical site with a reduced profile to minimize disruption of the surrounding tissues, nerves, and blood vessels.

In the context of vertebral reconstruction, balloons could be particularly useful. Vertebral reconstruction procedures, including percutaneous procedures such as kyphoplasty or vertebral body stenting, are used to correct a fractured vertebrae, a spinal deformity, or spinal instability, while intervertebral procedures, such as open surgery spinal fusion procedures, are used to correct the loss of disc height due to degenerative or herniated discs. Balloons using percutaneous procedures are not yet known to be commonly used in spinal fusion and intervertebral disc replacement procedures. Classic spinal fusion procedures are often effective to restore proper vertebral spacing and therefore relieve pressure on nerves and consequent pain, despite the huge open wounds and subsequent surgical trauma involved.

A problem with currently used fusion procedures occurs when two vertebral bodies are fused together because eventually the lack of an intervertebral disc between the two fused vertebral bodies overloads the adjacent intervertebral discs accelerating the degeneration of these adjacent discs. One treatment option is an intervertebral disc replacement, such as a prosthetic disc. This procedure is also used in patients with degenerative or herniated discs. A problem associated with a prosthetic disc is the vertebral bodies may need varying support in different locations. Pressure distribution on the damaged intervertebral disc may no longer be uniform, due to the years of damage to the spine that typically occurs before surgery is considered. Therefore, a prosthetic disc may not provide the necessary support to the vertebral bodies.

Another issue related to use of implants is that diseases, such as degenerative disc disease (DDD), are dynamic diseases: the intervertebral disc degenerates progressively and presents a variety of symptoms, and therefore treatment options. Disc degeneration is a normal part of the aging process and may not be an issue for a normal person. For an individual with DDD, however, a degenerated disc can cause severe chronic pain and lead to chronic debilitating conditions if left untreated. In some patients, DDD can be treated without surgery, but if non-surgical treatment options are unsuccessful, surgery is typically recommended. The surgical option selected for a patient depends on the stage of disc degeneration, i.e., early-, mid-, or late-stages of degeneration. Some examples of surgical procedures include: discectomy, corpectomy, fusion, dynamic stabilization, intervertebral disc arthroplasty (also called Artificial Disc Replacement (ADR)), and spinal decompression. Once traditional surgical procedures, such as fusion, are used to treat DDD, there is an increased rate of re-operation for patients to treat additional problems associated with DDD. One solution to this problem is to provide a method of treatment for DDD that allows a patient to retain mobility and preserve the range of motion to minimize the need for re-operation.

As one skilled in the related art would readily appreciate, there is a continuing need for new and innovative expandable medical implants and insertion devices directed toward the treatment of diseased and damaged bones and discs. More specifically, there exists a need for expandable medical implants that provide maximum support and ease of positioning within a cavity of bone and/or the disc space.

SUMMARY

To meet these and other needs, and in view of its purposes, the disclosure provides a multi-volume balloon for treating the clinical consequences of degenerative disc disease, vertebral body bone defects, and spinal motion segment instability. The balloon has a plurality of single volumes. The single volumes are each connected, directly or indirectly, to one another and contain a perforation site between at least two of the single volumes. Each single volume is individually adjustable and expandable such that (a) each single volume can contain a variable volume of contents, and (b) each of the plurality of single volumes can contain the same, or a different, amount and type of contents relative to another single volume.

The balloon of another embodiment has at least two pieces of material that are bonded together to form a balloon. The material of the balloon contains marks; the marks can be bonded together to form at least two compartments in the balloon.

The present application also provides several methods for treating the clinical consequences of degenerative disc disease, vertebral body bone defects, and spinal motion segment instability. In one embodiment, the method involves angling a single-volume balloon to create a multi-volume balloon. More specifically, the method includes the step of providing a single-volume balloon and at least one ring. The ring has two ends and the ends of the ring are set to a predetermined angle. The single-volume balloon is inserted into the ring. The ring containing the single-volume balloon is inserted into a cavity of a vertebral column, wherein the cavity is an intervertebral disc space or a vertebral body. The single-volume balloon is expanded, wherein the expansion of the single-volume balloon within the ring forms a multi-volume balloon with the predetermined angle of the ring determining the angulation of each volume of the multi-volume balloon.

The method of another embodiment involves aligning and stabilizing a vertebral column. The method includes the step of inserting a balloon-catheter containing a multi-volume balloon, wherein the multi-volume balloon is located at the distal end of the balloon-catheter, into a cavity of a vertebral column, wherein the cavity is an intervertebral disc space or a vertebral body. A first volume of the multi-volume balloon is expanded by inserting a fluid, wherein the expansion of the first volume restores height to the vertebral column. A second volume of the multi-volume balloon is expanded by inserting a solidifying material, wherein the solidifying material hardens after insertion to maintain the height restoration created by the expansion of the first volume.

The method of yet another embodiment involves inserting a balloon into a cavity of a patient. The method includes the step of rolling the balloon into a tubular shape. The balloon is then inserted into the cavity of the patient, wherein the cavity was cleared prior to insertion of the balloon. Once inside the cavity, the balloon is unfurled.

The present application also provides several kits for aligning and stabilizing bone. In one embodiment, the kit has at least one single-volume balloon and at least one ring. Each ring has two ends. The ends of the ring are set to a predetermined angle. When the single-volume balloon is inserted into the ring, inflating the single-volume balloon containing the ring creates a multi-volume balloon. The predetermined angle of the ring determines the angulation of each volume of the multi-volume balloon.

It is to be understood that both the foregoing general description and the following detailed description are exemplary, but are not restrictive, of the embodiments of the present application.

BRIEF DESCRIPTION OF THE DRAWING

The foregoing summary, as well as the following detailed description of illustrative embodiments, are best understood when read in connection with the accompanying drawing. It is emphasized that, according to common practice, the various features of the drawing are not to scale. On the contrary, the dimensions of the various features are arbitrarily expanded or reduced for clarity. Included in the drawing are the following figures.

DETAILED DESCRIPTION OF THE ILLUSTRATIVE EMBODIMENTS

Certain terminology is used in the following description for convenience only and is not limiting. The words "right," "left," "lower," and "upper" designate directions in the figures to which reference is made. The words "inwardly" and "outwardly" refer to directions toward and away from, respectively, the geometric center of the multi-volume balloon. The words "anterior," "posterior," "superior," "inferior," and related words or phrases designate preferred positions and orientations in the human body to which reference is made and are not meant to be limiting. The terminology includes the above-listed words, derivatives of those words, and words of similar import.

The clinical consequences of degenerative disc disease, vertebral body bone defects, and spinal motion segment instability can be treated by either restoring height to the intervertebral disc or by stabilizing the vertebral body. Treatment addresses a lesion zone "cavity" within the vertebral column. A cavity can include either the space previously occupied by the intervertebral disc, a space within a vertebral body, or both. The balloons reclaim both the disc space (i.e., they act as disc spacers) and the disc itself; the balloons are customized to provide the ideal shape to restore the anatomy of the patient. The balloons maintain the dampening function of the disc spacers and protect adjacent levels. In some embodiments, the balloons can assist in the fusion of any two bodies, preferably vertebral bodies.

In some embodiments, the balloon is a multi-volume balloon. A benefit of the multi-volume balloon approach to stabilization and fusion of vertebral bodies is that a surgeon, or caregiver, can adjust and specify the individual volumes of the multi-volume balloon to provide maximum stabilization within a cavity of the vertebral column, i.e., improved stabilization to reduce the risk of subsidence due to a better load distribution and improved manipulation options for an optimized spinal realignment. For example, if a degenerative disc results in a vertebral body sloping inferiorly on the left side of the patient's body, a single volume of the multi-volume balloon supporting that area need not be as inflated as a single volume of the multi-volume balloon on the right side of the patient's body. The embodiments of the multi-volume balloon provide for individualized, variable, and adjustable volumes of support from the multi-volume balloon. Further, a single volume balloon, for instance, may provide support in the center of the vertebral body, the weakest part of the bone. The multi-volume balloon provides support on an individualized basis but can target the peripheral edges of the vertebral bone to support the bone where it is most durable.

In other embodiments, the balloon, either a single volume balloon or multi-volume balloon, is made up of at least two pieces of foil or mesh bonded, or welded, together. The foil or mesh may be made of metal, polymers, or any other material discussed below. The bonding process, or welding process, can be accomplished by any method, such as, for example: ultrasonic welding, thermal welding using either a heat or light source, pressure welding (for example, by using clamps, jaws, chucks, or shrink tubing), swaging, joining, gluing, and stitching. The terms "bonded" and "welded" may be interchangeably used herein. The benefit of using materials such as these bonded together is that it increases the flexibility of the shape of the balloon. In some embodiments, the balloon may be made up of a combination of foil and mesh materials with different thicknesses. This structure provides for superior dilatation, load-bearing, permeability for primary fixation/adjacent augmentation, and degradation properties over balloons in the prior art.

The balloons may be used to treat any bone or disc with an interior lesion or cavity sufficiently large to receive the balloon. Non-limiting examples of bones that are suitable candidates for anatomical restoration using the device and method of the embodiments include vertebral bodies, the medullary canals of long bones, the calcaneus and the tibial plateau. The balloon can be designed and adapted to accommodate particular bone or disc anatomies and different cavity shapes, which may be made in these and other suitably large bones.

The material of the balloon is selected based on the intended purpose of the balloon. For example, if one of the volumes of the balloon is used to lift a vertebral body by occupying the intervertebral disc space, or provide a cushioning/dampening effect, the material may be more elastic in order to permit variances in volumes as needed. The balloon may also be made of a rigid or non-elastic material, such as, for example, foil or foil coated with a protective material. The balloon may be thick-walled to contain liquids for an extended period of time, i.e., beyond the lifting of a vertebral body or disc. The multi-volume balloon may be designed and configured to be deployed and remain in the bone cavity for an extended period of time. Balloons can be made of any suitable material to provide for inflation and/or stabilization, such as, for example, foil, mesh, silicone rubber, elastomeric rubber, polyether ether ketone (or PEEK), polyether ketone ketone (or PEKK), polyethelyene (or PE), polyurethane (or PU), polycarbonate urethane (or PCU), polyethylene terephthalate (or PET), thermoplastic polyurethane (or TPU), etc. Any one of a diverse set of polymers is preferred. Balloon materials for temporary use may include polyamides (or PA) and co-polymers thereof, e.g., polyetherblock-amide (or PEBA, Pebax), allowing for suitable balloon material compliance tuning. In some embodiment, the balloon can be a circuit board containing printed black marks, wherein the marks are bonded together upon exposure to heat-generating light: the light is absorbed only by the marks (or black lines), generating local heat and hence bonding at that site, otherwise the light is transmitted through the substantially transparent balloon. A balloon made with softer, more elastic substances is better for correcting load distribution while a harder balloon is better for realignment and space maintenance. In another embodiment, the balloon may be biologically resorbable. Biologically resorbable balloon materials may include polylactides, magnesium alloy components, etc.

Once filled, the balloon is allowed to remain within the intervertebral disc space or bone for a prescribed period of time or perhaps indefinitely. The duration of time that the balloon remains within the bone may depend upon specific conditions in the treated bone and the particular objective sought by the treatment. When the balloon is implanted for a short period of time, it functions as an instrument in creating space, or lifting the vertebral body, hence enabling load bearing and/or sharing along the spinal column axis. Alternatively, the balloon functions as an implant when it remains in the patient for longer periods of time. The balloon may remain within the cavity for prescribed periods of time that include, for example, an hour, a day, several days, weeks, months, or years, or even may remain within the bone permanently.

The balloon content material can be any one or a combination of a number of: liquids, such as, for example, water, saline solutions, radiopaque contrast medium solutions; elastic-type contents, such as, for example, elastomers (especially silicone-based), hydrogels, silicone; rigid contents, such as, for example, polymethyl methacrylate (PMMA), hydroxylapatide-based materials, calciumphosphate-based materials, and other bone cements; particles, such as, for example, bone, polymers, bone chips in a liquid; and bioabsorbable materials. Bone cements may provide a rigid construct or be elastic; both the rigidity and elasticity may be reached in-situ via a chemical reaction, such as polymerization or crystallization reactions. Solidifying materials may also be used to provide a rigid construct, such as, for example: polymers, crystalline solids, elastomers, and glass. Aqueous liquids (such as saline, contrast media, mixes thereof, etc.) as well as elastomers provide a dampening cushion. The dampening cushion provided by the device is designed to restore any weakened/damaged structures that are adjacent to the balloon, as well as to protect any intact/healthy structures that are adjacent to the balloon. A problem with the currently used devices, which fuse two vertebral bodies together, is eventually the fused vertebral bodies create the same issue in the nearby discs because the fused bodies compensate for the lack of an intervertebral disc by overloading the nearby discs. In contrast, embodiments of the balloon provide a dampening effect by creating a cushion and restoring the adjacent vertebral bodies.

In an alternative embodiment, some compartments of the balloon may provide a dampening cushion and other compartments provide a rigid construct. In this embodiment, the dampening compartments may be filled with a greater volume of contents than the rigid compartments. For example, if the cavity experiences a sudden increase in pressure and is compressed, the greater filled dampening compartments absorb the shock of the increase in pressure and the lesser filled rigid compartments prevent the height of the cavity from decreasing below the height of the rigid compartment.

The content material can also be a two-component mixture, for example, bone chips with a hardening agent. Liquids are possible, but not recommended because liquids render critical both seals and valves. A thick-walled balloon is recommended if the balloon will be filled with liquid and implanted for an extended period of time. A seal, or bonding, according to an embodiment creates a leak-proof closure to prevent the contents of the balloon from leaking out. One embodiment involves inserting a liquid into the balloon, where the expanded balloon is used as an instrument to lift the vertebral body to a desired height. The liquid is then removed from the balloon (i.e., balloon deflation) and the balloon is removed (i.e., balloon retrieval) from the patient. Once height is restored, a bone cement, a cage, or any other device can be inserted to occupy the space created by the balloon, provided there is no collapse of the created space.

In some embodiments, the content material can be heated above body temperature (about 98.6° F.) so that it hardens faster (approximately 140° F.-160° F.); applied heating accelerates hardening of the content material. The content material is heated, rather than the entire balloon or even the walls of the balloon. An example of a preferred content material that can be selectively heated includes PMMA. The heat can be selectively applied to the content material of discrete volumes of the balloon. A heat probe can be affixed to the device to accelerate the chemical reaction in order to harden the contents of the balloon. The heat can be applied after insertion of the multi-volume balloon into the patient. A benefit is that once the balloon is filled, it can remain within the body of the patient. The content material hardens, either by body temperature alone or by the application of additional heat to harden the contents within the balloon; this eliminates the concern of leakage of the material from the balloon because it is a hardened material, especially if the balloon is to remain within the body for an extended period of time. The contents of the balloon must be biocompatible because of potential mechanical degeneration or tearing of the balloon itself, if implanted for the long term.

Alternatively, the entire balloon is heated because the heat may not alter the balloon wall while the contents are hardened.

The content material is provided under precise pressure and volume control. In a preferred embodiment, the balloon is inflated directly against the bone to be restored. This would cause the deployed balloon to press the damaged bone into a configuration that reduces fractures and restores the anatomy of the damaged bone.

A method according to an embodiment includes customizing the contents of the balloons based upon the stage of disc degeneration in a patient or based on the progression of degeneration. In early-stage degeneration, it is preferable that the content material be a saline solution, hydrogel, elastomer (or elastomer cement), or silicone-type material. In early stages of degeneration, the method provides a stabilization of the treated level and an adjacent level of protection. In mid-level stages of disc degeneration, preferred content material includes bone cements; rigid compound materials, such as, for example, hydroxylapatide-based materials and calciumphosphate-based materials; and particulate materials. In mid-level stages of degeneration, the method provides for a rigid construct to allow for bony fusion to occur. In late stages of disc degeneration, preferred content materials include bone cements and rigid compound materials, such as, for example, hydroxylapatide-based materials and calciumphosphate-based materials. In late stages of degeneration, the method provides for a rigid filling that completely covers the endplate of the vertebral body and, due to a permeability towards the vertebral body endplates, allows for penetration of filler through the endplates into the vertebral bodies that results in primary stabilization and augmentation. Determining the necessary contents may be difficult because of the progression of disc degeneration from early-, to mid-, to late-stages of degeneration. One purpose of the method is to match the contents of the balloon to the progression of the disease or disc degeneration. The content material in the balloon might be removed and replaced with a different filler as the disease progresses.

In addition, the outer surface of the balloon may be treated with a coating or texture to help the balloon become more integral with the surrounding bone matter or to facilitate acceptance of the balloon by the patient. The selection of balloon materials, coatings, and textures also may help prevent rejection of the balloon by the body. Likewise, the outer surface of the balloon may be treated with a coating or texture to help the balloon become more puncture and tear resistant. The inner surface of the balloon likewise may be textured or coated to improve the performance of the balloon. For instance, the inner surface of the balloon may be coated or textured to increase adhesion between the balloon wall and the material inside or, alternatively, to prevent contact between the balloon wall and the content material if, for example, the balloon wall material and contents were physically or chemically incompatible.

The balloon is inserted into a bone cavity or disc space that has been prepared to allow the balloon to be placed in the disc space or near the damaged bone. In some embodiments, the cancellous bone tissue and bone marrow inside the bone and in the area to be treated may be cleared or compressed away from the region in advance of deploying the balloon. Clearing the treated region may be accomplished by either shifting or relocating the cancellous bone and marrow to untreated regions inside the bone, or by removing the materials from the bone by using a reamer or some other device. In embodiments where the space is cleared before insertion of the balloon, less resistance is needed to unfurl or expand or otherwise deploy the balloon. In the disc space, alternatively, a discectomy can be performed to remove the intervertebral disc. These methods are particularly useful in embodiments where devices to promote fusion are inserted after the balloon. In some embodiments, the balloon is the device that is inserted to promote fusion.

In addition, the bone cavity or disc space may be irrigated or aspirated to permit balloon implantation and to create an environment suitable for bone growth. Preferably, the aspiration would be sufficient to remove cancellous bone or disc material within the region to be restored. More preferably, a region exceeding the extent of the fully deployed balloon by about 2 mm to 4 mm would be aspirated in this manner. Clearing the cavity of substantially all bone marrow near or within the treated region may prove especially useful for restoring the bone and incorporating the balloon as a prosthetic device to remain in the cavity. Pre-clearance of material within the cavity provides for decreased resistance when the balloon is inflated within the cavity. U.S. Pat. No. 6,679,886 to Weikel, et al. entitled "Tools and methods for creating cavities in bone" (the contents of which are incorporated by reference) describes a method for creating cavities in bone. In another embodiment, the intervertebral disc or disc space does not need to be cleared out before placing the balloon in the disc space. In this embodiment, a guide wire, preferably a pre-bent guide wire, guides the balloon to the disc space and expands the balloon inside the lesion site, compressing any tissue or bone around the balloon.

A challenge in the art is a posterior approach to the vertebral disc that has a very limited path during surgery, especially if the tools used by the surgeon are all straight tools. The surgeon must navigate around corners and has a difficult time gaining access to the entire vertebral disc and placing any device in the proper location of the intervertebral disc. Therefore, the method involves the steps of introducing the balloon in a deflated state, with a reduced profile, and then inflating the balloon once it is delivered to the desired location. Still another solution to this problem is achieved by inserting the device in a deflated state with small diameter equipment; therefore, a surgeon can use a posterior approach to insert the balloon and avoid the limitations of an anterior approach.

In some embodiments, a cavity may be pre-created by inserting a balloon, such as a simple spherical balloon, into the cavity of the patient. In this embodiment, the balloon is inserted into the patient, the balloon is expanded, thus creating the cavity, and removed. A balloon according to this embodiment is then inserted into the pre-created cavity and can be inserted, unfurled, expanded, and/or otherwise deployed into the cavity of the patient. The balloon meets much less resistance in the pre-created cavity than it would in a cavity that is filled with tissue, cartilage, bone, etc.

Note that access is paved for the balloons using a posterior minimally invasive surgery (MIS) approach via a 3 mm to 10 mm diameter cannula, or even using a posterior percutaneous approach of only 1 mm to 4 mm. A device inserted via a posterior approach is limited in size by the interval between the nerve roots. Therefore, the balloon is expanded from within the intervertebral space or cavity to reduce potential trauma to the nerve roots and yet still allow restoration of disc space height. Alternatively, a surgeon can use a lateral, anterior-lateral, or anterior approach to introduce the balloon because the balloon is introduced in a deflated state and the tools are minimal in diameter and therefore the risk of an interference with sensitive soft tissues such as nerves is reduced.

In some methods, the balloon can be rolled into a tubular shape outside the body of the patient; the shape of the balloon is selected, or the balloon is bonded into its shape and connected to the other components of the balloon-catheter before it is rolled into a tubular shape, and kept in that furled up state by sliding a cover sleeve onto it. The balloon is then inserted into the body through a working sleeve or other tube-shaped cannula, and then unfurled once inside the body, or appropriate cavity, of the patient. Alternatively, the balloon can be rolled around a guide wire outside the body of the patient and then unfurled once inside the body, or appropriate cavity, of the patient. This method allows the balloon to be inserted with a low profile, in a tubular shape, and then unfurled into a flat shape because the balloon is not yet inflated. The rolled balloon can be inserted into a cavity that is pre-created or cleared, according to any of the methods described above, to encounter less resistance when it is unfurled or expanded. The balloon, or the individual compartments of the balloon, are then inflated with any of the contents necessary to restore the proper anatomy of the patient.

FIG. 1 is a perspective view of a kit used to form a multi-volume balloon from a single-volume balloon. A single-volume balloon 2 is provided in the kit along with at least one ring 5. Preferably, the kit includes a variety of rings 5 of different geometric characteristics. FIG. 1A shows that the example ring 5 has an angle 7 on its right end and an angle 9 on its left end. Angle 7 and angle 9 of the ring 5 determine the orientation and angle of each volume of a multi-volume balloon; the volume takes the angulation of the ring 5. Angle 7 and angle 9 of the ring 5 can be set to a predetermined angle. By "predetermined" is meant determined beforehand, so that the predetermined angle must be determined, i.e., chosen or at least known, in advance of inserting the ring 5 onto the single-volume balloon 2. As is shown in FIG. 1B, FIG. 1C, FIG. 1G, FIG. 1I, and FIG. 1K a multi-volume balloon 10 has ring 5 with angle 7 and angle 9. Once ring 5 is inserted onto the single-volume balloon 2, multi-volume balloon 10 is created.

Figure 1A:
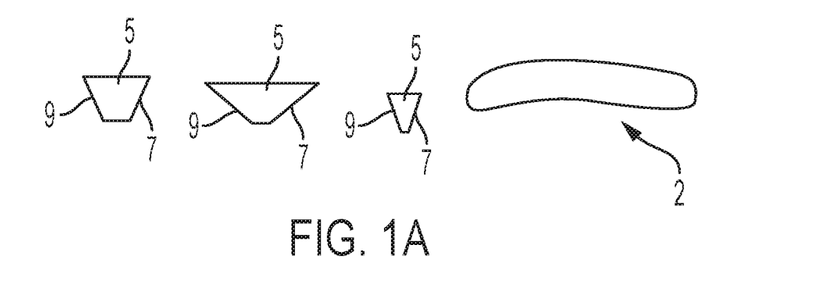
FIGS. 1A, 1B, 1C, 1D, 1E, 1F, 1G, 1H, 1I, 1J, and 1K show perspective views of a kit used to form a multi-volume balloon from a single-volume balloon according to an embodiment.

In one embodiment, the ring 5 can be adjusted once the single-volume balloon 2 is expanded and the multi-volume balloon 10 is formed. In another embodiment, the ring 5 does not move once mounted and the multi-volume balloon 10 is formed. In yet another embodiment, the kit is provided with the ring 5 pre-mounted onto the single-volume balloon 2.

Figure 1B:
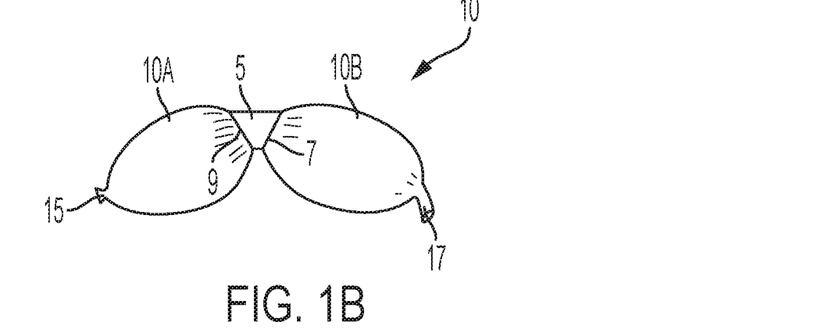
Figure 1C:
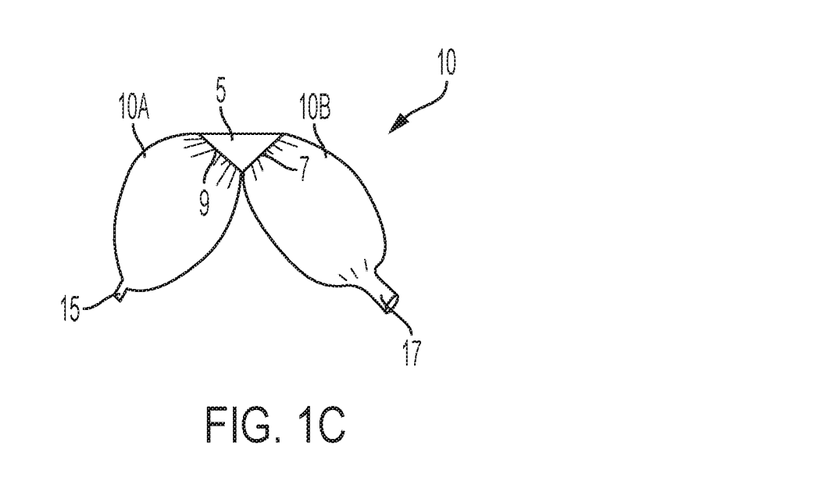

As is shown in FIGS. 1B and 1C, multi-volume balloon 10 is made up of two volumes, volume 10A and volume 10B. The amount of contents of volume 10A and volume 10B depend upon the location of ring 5 along the length of the single-volume balloon 2 and the angle 7 and angle 9. A surgeon can determine the amount of volume needed in the multi-volume balloon 10 either before or during surgery. The ring 5 can be adjusted to vary the angle and capacity of volume 10A and volume 10B of the multi-volume balloon 10. In accordance with this embodiment, more than one ring 5 can be placed on the single-volume balloon 2 to create more than two volumes. As shown in FIG. 1A, the size of ring 5 and angles 7 and 9 can be selected to meet the needs of a particular patient and application. The number of volumes that form multi-volume balloon 10 can vary based on the number of rings 5. FIG. 1E is a multi-volume balloon 10 that has three volumes, 10A, 10B, and 10C; FIGS. 1I and 1G are multi-volume balloons 10 with five volumes and six volumes, respectively.

FIG. 1B, FIG. 1C, FIG. 1E, FIG. 1G, and FIG. 1I are perspective views of multi-volume balloon 10. As is shown in FIG. 1B, FIG. 1C, FIG. 1E, FIG. 1G, and FIG. 1I, multi-volume balloon 10 has a closed end 15 and a sealed end 17. Closed end 15 is distal to the surgeon and/or insertion instrument and prevents the release of contents from the multi-volume balloon 10. Sealed end 17 is proximal to the surgeon and/or insertion instrument. Single volume balloon 2 is inflated, and creates multi-volume balloon 10, by connecting inflation end 18 with an insertion device, such as, for example, an injection syringe (e.g., a pressure syringe with a manometer that takes volumetric readings while multi-volume balloon 10 is being inflated). Contents that are used to inflate multi-volume balloon 10 through inflation end 18 depend upon the specific needs of the patient and can include non-rigid or rigid contents, as described above. Temporary implants, such as a multi-volume balloon 10, are filled with saline, aqueous, or other non-rigid contents after inflation of the multi-volume balloon 10. Inflation end 18 of the balloon is then disconnected from the insertion instrument and sealed end 17 created by sealing the proximal end of the multi-volume balloon 10 with a valve, for example, to prevent the release of contents from the multi-volume balloon 10. Permanent implants, such as a multi-volume balloon 10, are filled with hardened bone cement, e.g., PMMA or other rigid contents. Inflation end 18 of the balloon 10 is then disconnected from the insertion instrument and sealed end 17 is created by severing and disconnecting the proximal end of the multi-volume balloon 10 from the insertion instrument.

Figure 1D:
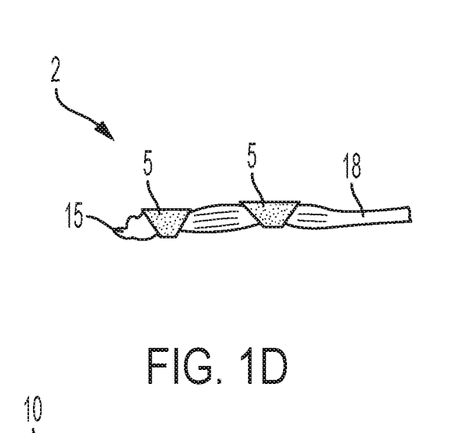
Figure 1E:
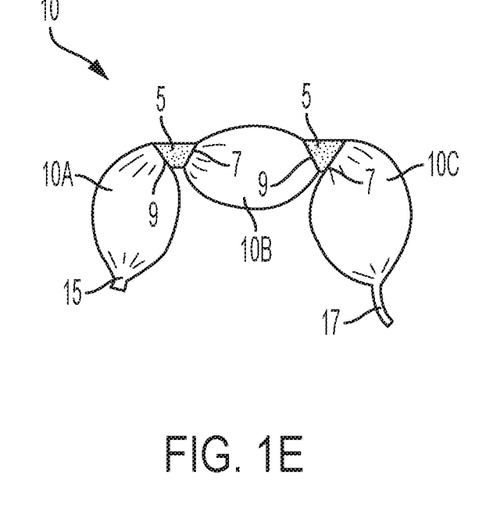
Figure 1F:
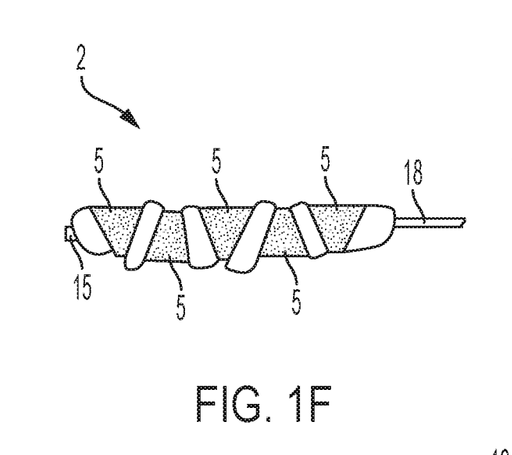
Figures 1G, 1I:
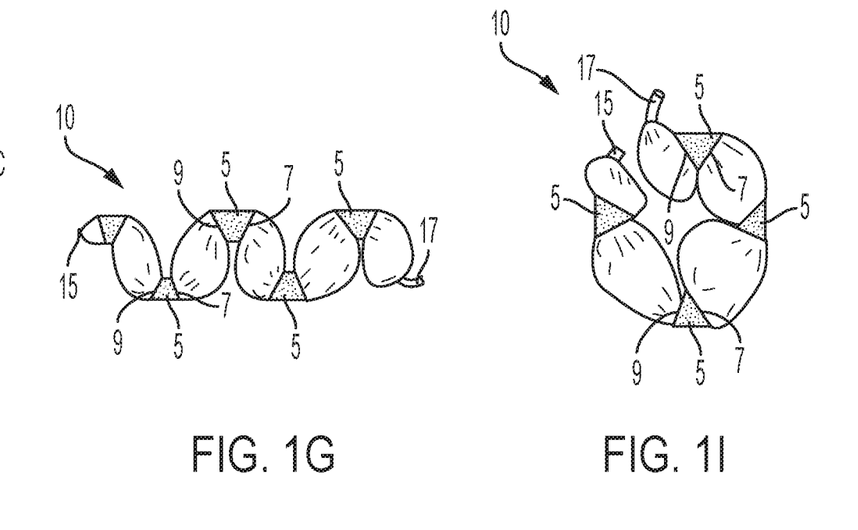
Figure 1H:
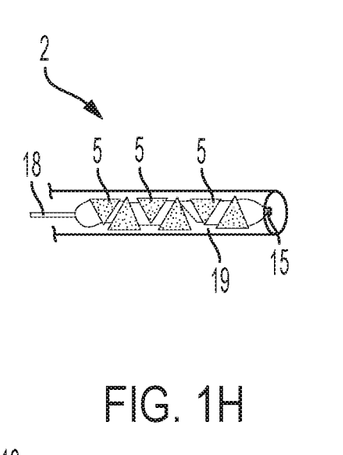

FIG. 1D, FIG. 1F, and FIG. 1H are perspective views of a single volume balloon 2 with varying numbers of rings 5 to create different numbers of volumes of the multi-volume balloon 10 after the balloon is inflated. An insertion instrument is connected to the proximal inflation end 18. Distal closed end 15 is closed before inserting contents into the single volume balloon 2 to prevent the contents from being released. And the contents are inserted into the single volume balloon 2 to create the multi-volume balloon 10. Angle 7 and angle 9 of the ring 5 provide for varying shapes of multi-volume balloon 10.

Inflation of the single volume balloon 2 shown in FIG. 1D results in a multi-volume balloon 10 having a kidney, or banana shape, shown in FIG. 1E. In another embodiment, inflation of single volume balloon 2 shown in FIG. 1F results in a multi-volume balloon 10 having a snake-like form, shown in FIG. 1G. In yet another embodiment, single volume balloon 2, shown in FIG. 1H, is covered with a cover sleeve 19 that constrains the single volume balloon 2. As contents are inserted through inflation end 18 and into the single volume balloon 2, shown in FIG. 1H, the cover sleeve 19 initially constrains the expansion of the single volume balloon 2. The closed end 15 of the single volume balloon 2 unwinds as it exits the cover sleeve 19 at the distal end. As the single volume balloon 2 exits the cover sleeve 19 it is then unconstrained by the cover sleeve 19, and the multi-volume balloon 10, as is shown in FIG. 1I, is formed having a twisted configuration.

In some embodiments, the ring 5 is made of a metal, such as stainless steel or titanium, that can act as a marker. In another embodiment, ring 5 is made of a material to act as an x-ray marker, such as a cobalt chrome alloy. In another embodiment, the ring 5 is made of a polymer, rendering the ring more compatible for magnetic resonance imaging (MRI) technologies. It is also possible to make the ring 5 of PEEK. PEEK is a semi-crystalline thermoplastic with excellent mechanical and chemical resistance properties that are retained to high temperatures. Therefore, PEEK is considered an advanced biomaterial used in many medical implant applications.

The ring 5 can comprise a one-way valve, namely, that allows a liquid to flow only in one direction and not the opposite direction. A simple membrane can also function as a one-way valve. The specific one-way valve can be selected, as within the skill of an artisan, to meet the needs of a particular patient and application.

Figure 1J:
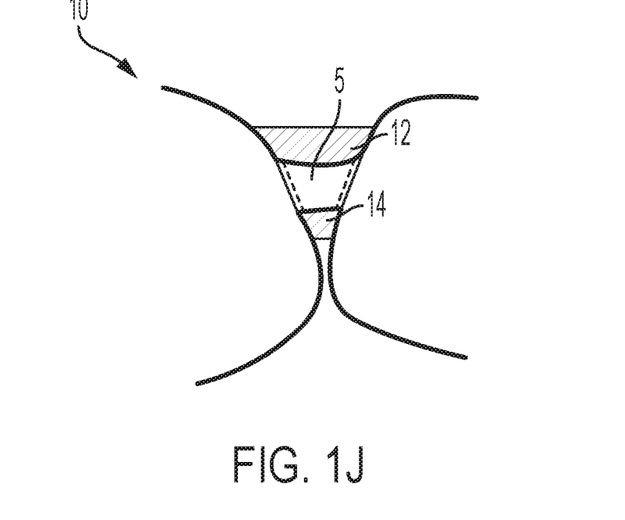
Figure 1K:
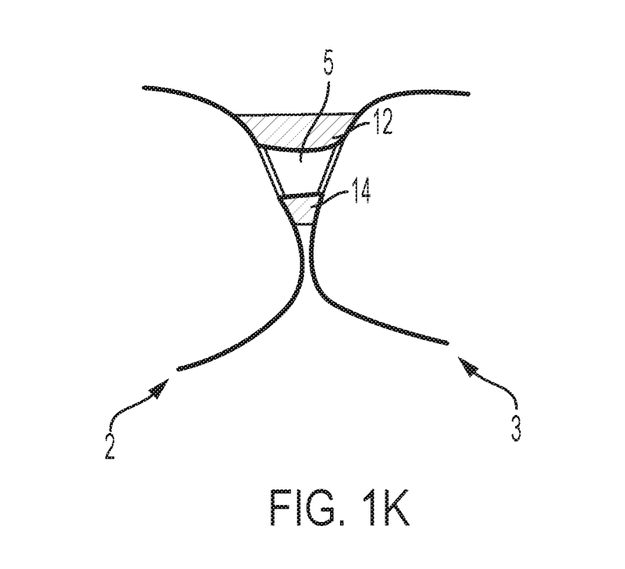

In order to further reduce the diameter of the balloon, the balloons can be attached to the ring 5 by welding, gluing, stitching or any other bonding method known in the art. As is shown in FIG. 1J, ring 5 is bonded to multi-volume balloon 10 at a bonding site 12 and a bonding site 14. In an alternate embodiment, as is shown in FIG. 1K, single volume balloon 2 and a single volume balloon 3 are bonded to ring 5 at bonding site 12 and bonding site 14.

Figure 2A:
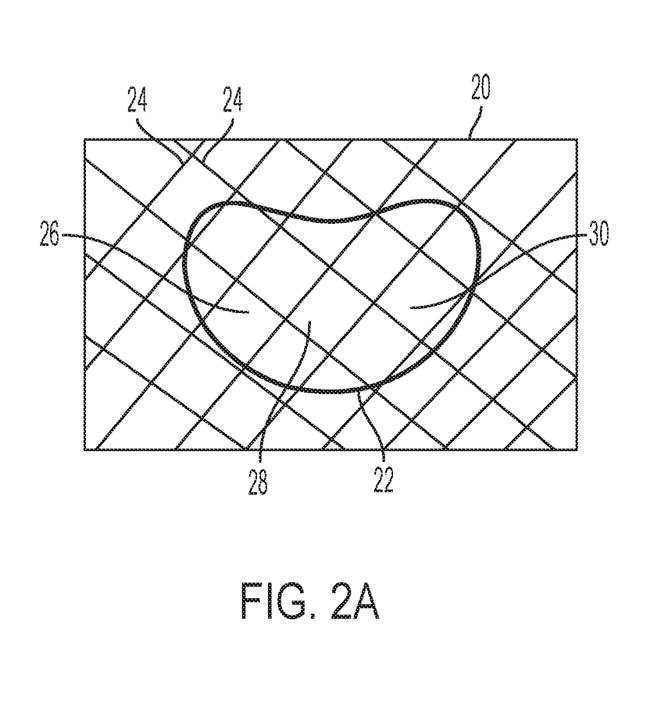
FIGS. 2A and 2B show perspective views of a single or multi-volume balloon according to another embodiment.
Figure 2B:
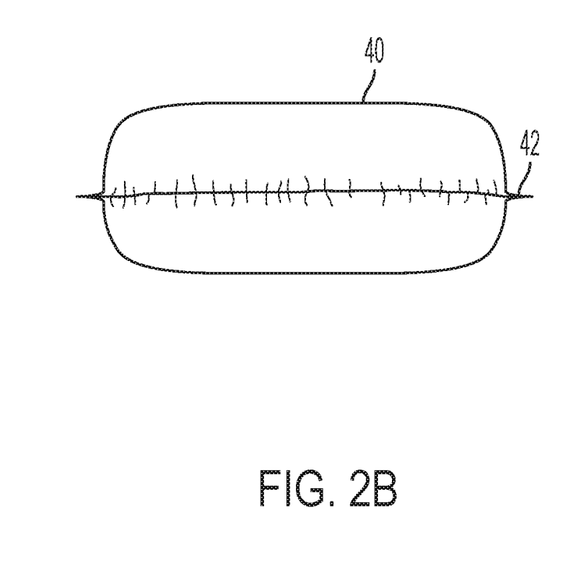

FIG. 2A is a top view and FIG. 2B is a side view of a single or multi-volume balloon according to another embodiment. FIG. 2A shows two layers of uncut foil 20 placed on top of each other. In FIG. 2A the two layers of uncut foil 20 are in a rectangular shape, but the shape of the uncut foil 20 can be any shape, such as, for example, circular, triangular, square, or oval. The two layers of uncut foil 20 are scored with marks 24. The intersection of the marks 24 can create individual volumes 26, 28, 30 throughout the uncut foil 20. A balloon 22 is created from the uncut foil 20 by bonding the two layers of the uncut foil 20 together. The layers can be bonded together by methods known in the art, such as, for example, welding, heat, glue, stitching, friction, laser beam technologies, laser beam technologies with an additional absorption medium, ultrasonic technologies, and energy beam methodologies. Balloon 22 can be cut out of the uncut foil 20 in any shape that is necessary to fill a cavity of a patient. The perimeter of the balloon 22 is bonded together, as discussed above. In some embodiments, the balloon 22 is manufactured in a desktop printer-like device. The uncut foil 20 can be made of polymers or metal. In some embodiments, the uncut foil 20 can be made of a mesh material that can be made of polymers or metal to allow for permeability. The metal can consist of a metallic thin film, preferably made from shape-memory alloy, such as, for example, nitinol. In another embodiment, the uncut foil 20 can be a circuit board containing printed black marks, wherein the marks are bonded together upon exposure to heat-generating light; the light is absorbed only by the marks (or black lines), generating local heat and hence bonding at that site, otherwise the light is transmitted through the substantially transparent foil.

This embodiment can be customized to fill the cavity of a patient. The compartments of the uncut foil 20 or balloon 22, created by the marks 24, can be selectively filled or left empty, depending on the specific needs of the patient. This provides for a varying topography and infinite possibilities for what compartments to fill, which to leave empty, and what contents to provide to each of the compartments.

The compartments may be filled with different materials, depending upon the needs of the patient. For example, some compartments (for example, compartments 26 and 30) may be filled with water, saline, contrast media solution, or similar type substances, to provide for a cushioning or dampening effect ("cushioning compartments"). Other compartments (for example, compartment 28) may be filled with a hard material, such as a polymer or bone cement, to provide support and height and act as a stopper ("support compartments"). In this embodiment, the cushioning components may contain more material than the support compartments so that if, the cavity experiences sudden pressure, the cushioning compartments provide flexibility to dampen the shock, while the support compartments act as a stopper to prevent the height of the balloon 22 from minimizing below the height of the support compartment. The compartments can be filled once the balloon 22 is inserted into the cavity of the patient.

In another embodiment, the compartments located closest to the perimeter of the balloon 22 can be support compartments, as discussed above, and the compartments in the interior of the balloon can be cushioning compartments. In this embodiment, the support compartments provide support and height, as discussed above, but also act as a stopper, or boundary, for the filing in the cushioning compartments. The support compartments are not limited to the perimeter of the balloon 22, but can be arranged in any pattern in the balloon to act as a boundary for the filling in the cushioning compartments.

In some embodiments, the contents of the compartments may be changed over time. A compartment that was previously empty can be filled at a later time, or a compartment that was a cushioning compartment can have the contents removed, filled with a hard material, and be converted to a support compartment.

FIG. 2B is a side view of an alternative embodiment. In FIG. 2B, the marks 24 of the uncut foil 20 did not create individual compartments, but rather after balloon 22 was bonded, a single volume balloon 40 was created. A bonding 42 is the site where the uncut foil 20 was bonded along the shape outlined for the balloon 22.

The layers of the uncut foil 20 can be bonded either during manufacturing, or before insertion into a patient or even during surgery, allowing for intra-operative customization of the shape and size of the implant. In this embodiment, the patient may undergo a pre-surgical evaluation to determine the size of the balloon 22 needed to fill the cavity. In some embodiments, the uncut foil 20 or balloon 22 can be curled around a guide wire or insertion instrument and guided to a cavity of the patient. In this embodiment, the balloon 22 is not inflated before insertion. This allows the balloon to be inserted with a low profile. The uncut foil 20 or balloon 22 is then unfurled within the cavity; the balloon 22 may then be bonded from the uncut foil 20. The surgeon then determines what individual compartments to fill, or alternatively, the whole balloon 40 may be expanded, in order to provide selective lifting power and height restoration, depending on the needs of the patient.

The anatomical situation of the patient, and the varying possibilities for filling the compartments of the uncut foil 20, provide an array of three dimensional shaped balloons that are individually created for each patient.

Figure 3:
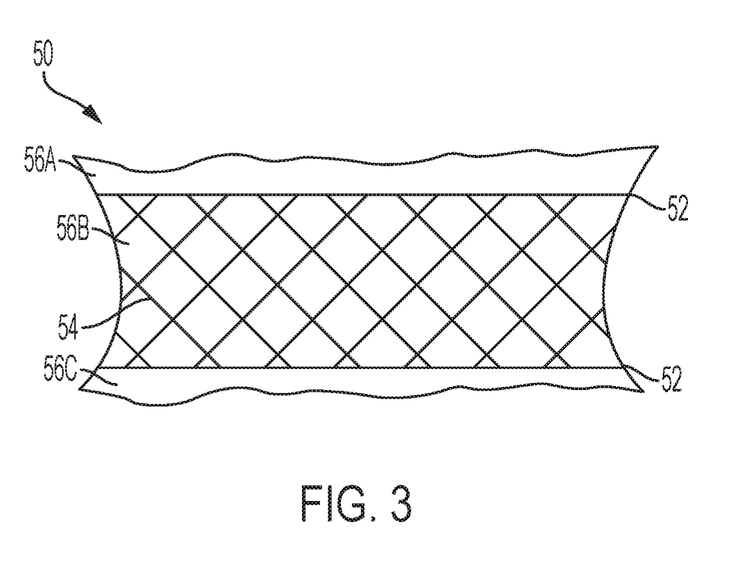
FIG. 3 shows a perspective view of a single or multi-volume balloon according to another embodiment.

FIG. 3 is a perspective view of a single or multi-volume balloon according to another embodiment. A multiple-bond balloon 50 is created by bonding together three or more sheets of foil 56A, 56B, 56C along the bonding sites 52. In some embodiments, the multiple-bond balloon 50 is manufactured in a desktop printer-like device. The layers can be bonded together by methods known in the art, such as, for example, heat, glue, stitches, friction, pressure, laser beam technologies, laser beam technologies with an additional absorption medium, ultrasonic technologies, and energy beam methodologies. The multiple-bond balloon 50 provides for an array of 3-dimensional free shaped balloons that are not limited to an oval or spherical shape of a single volume, or the shape of a single-bond balloon. The foil sheets 56A, 56B, 56C of multiple-bond balloon 50 can have marks 54 that create individual compartments as described with reference to FIG. 2A and FIG. 2B above. The compartments can be selectively filled to create a unique anatomic shape and consistency as described above. Each compartment can be either unfilled or filled; the filled compartments can be filled with material that provides either a cushioning or support effect for the patient. In some embodiments, the compartments can be filled in a maze-like fashion, e.g., located on a second plane that is parallel to the balloon plane.

FIG. 4A, FIG. 4B, FIG. 5A, and FIG. 5B are perspective views of a multi-volume balloon according to additional embodiments. These figures show a multi-volume balloon 80 with a lifting volume 82 and a filling volume 84. In some embodiments, the locations of lifting volume 82 and filling volume 84 can be reversed. The multi-volume balloon 80 may comprise more than one lifting volume 82 and more than one filling volume 84 to obtain a desired height and stabilization. According to this embodiment, lifting volume 82 is filled with a substance that is easy to remove, such as saline. The lifting volume 82 is filled to create height (e.g., re-create the height of a disc space) or lift any fractures in a cavity of bone. Once the desired height is achieved, the contents inside lifting volume 82 are removed. Contents are then injected into filling volume 84 to maintain the volume created by lifting volume 82. Preferred contents for insertion into filling volume 84 include those that would make filling volume 84 rigid, such as a polymer or bone cement.

The combination of separate lifting volume 82 and filling volume 84 offers significant advantages. One advantage is better load distribution. Another advantage is better control when lifting and re-creating the disc space. In summary, the combination of two, separate volumes having different functions is better than using one volume to achieve both functions (which inherently requires tradeoffs).

Figure 4A:
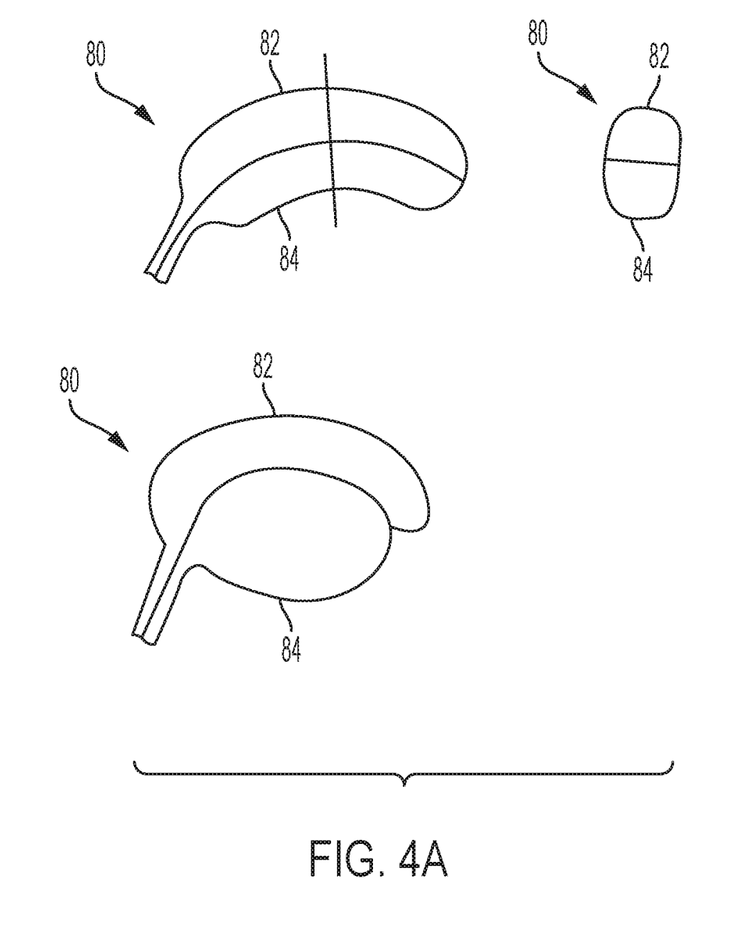
FIGS. 4A and 4B are perspective views of a multi-volume balloon according to another embodiment.
Figure 4B:
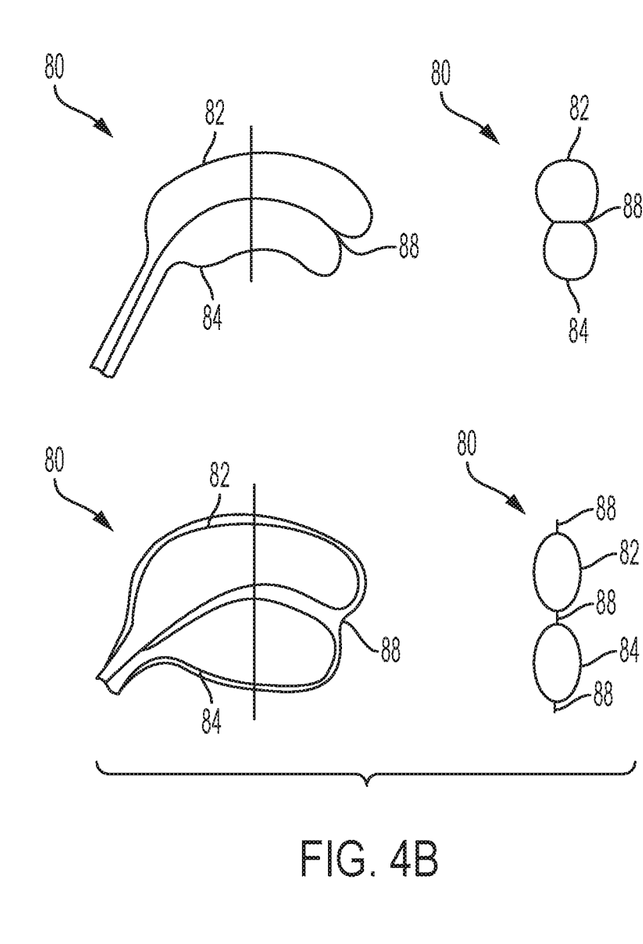

FIG. 4B shows lifting volume 82 and filling volume 84 separated by a bonding site 88 that is created by two foils bonded together. The foil layers can be bonded together by methods known in the art, such as, for example, heat, glue, friction, laser beam technologies, laser beam technologies with an additional absorption medium, ultrasonic technologies, and energy beam methodologies. The multi-volume balloon 80 in FIG. 4B is formed of a foil material. The foil material provides a free-form balloon for the surgeon. In other embodiments, the multi-volume balloon 80 is formed of a mesh material.

Figure 5A:
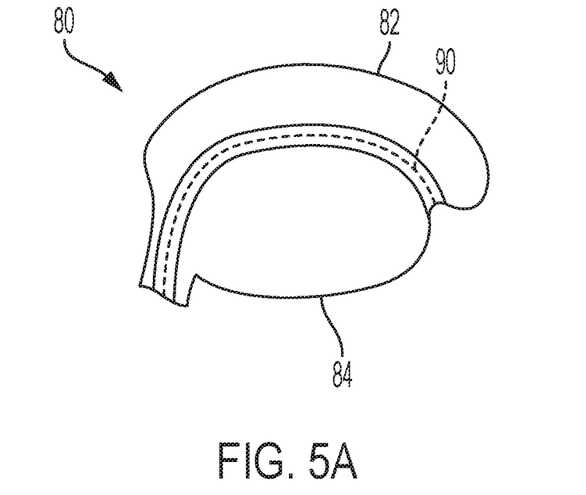
FIGS. 5A and 5B are perspective views of a multi-volume balloon according to another embodiment.

FIG. 5A shows a multi-volume balloon 80 that contains lifting volume 82 and filling volume 84 separated by a perforation 90. Perforation 90 provides a controlled break for separation of lifting volume 82 from filling volume 84 at a pre-determined breaking point.

Figure 5B:
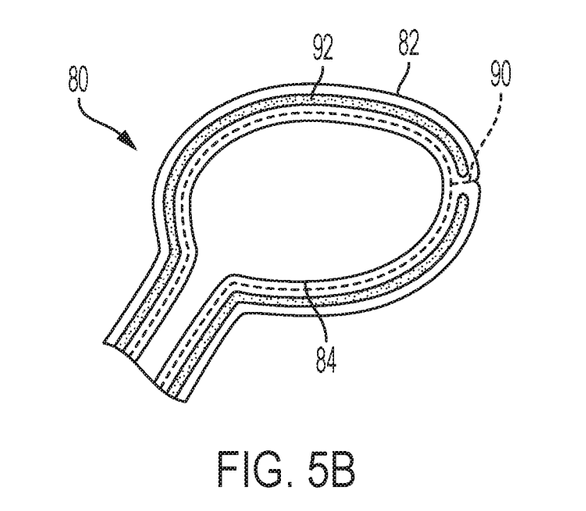

FIG. 5B also contains a perforation 90 to permit a controlled break between lifting volume 82 and filling volume 84. Multi-volume balloon 80 as shown in FIG. 5B further contains a guidewire 92 that is attached to multi-volume balloon 80. Guidewire 92 provides for control in the insertion and placement of multi-volume balloon 80 in a cavity of bone. Guidewire 92 can be removed by tearing off perforation 90. In some embodiments, guidewire 92 can include a sensor or light source.

In alternative embodiments, the locations of filling volume 84 and lifting volume 82 can be reversed. Any lumen of the multi-volume balloon 80 shown in FIG. 5A and FIG. 5B can be the lifting volume or the filling volume. It may not be predetermined which volume is the filling volume 84 and the lifting volume 82. All volumes of the multi-volume balloon 80 are finable with any contents discussed above.

Lifting volume 82 creates additional space in the cavity for bony fusion and can be removed, but does not have to be removed, from the multi-volume balloon 80. In alternative embodiments, lifting volume 82 can be filled to create space. Subsequently, filling volume 84 can be filled with any contents as discussed above and lifting volume 82 can be emptied. At any time point later, lifting volume 82 can be filled with a different content to provide support or cushioning to the patient, or removed by tearing at the perforation 90, dependent upon the patient's needs.

Although the invention has been described with reference to certain preferred embodiments, it should be kept in mind that the scope of the invention is not limited to these embodiments. The balloon can be modified or extended to accommodate particular formulations of balloon construction materials or fabrication techniques. Similarly, the number and spacing of the single volumes of the multi-volume balloon may be changed to better accommodate the cavity. Different balloon materials and surface coatings, or outer layers of different materials or surface coatings, may also be applied to the balloon to facilitate a smaller balloon profile for deployment. The embodiments above can also be modified so that some features of one embodiment are used with the features of another embodiment. One skilled in the art may find variations of these preferred embodiments which, nevertheless, fall within the spirit of the invention, whose scope is defined by the claims set forth below. It is also expressly intended that the steps of the methods of using the various balloons disclosed above are not restricted to any particular order.

What is claimed:

1. A multi-volume balloon for treating clinical consequences of degenerative disc disease, vertebral body bone defects, and spinal motion segment instability comprising a plurality of single volumes connected to one another along a perforation site located between two adjacent single volumes that provides a pre-determined breaking point between the single volumes, wherein each single volume is individually adjustable and expandable such that (a) each single volume can contain a variable volume of contents, and (b) each of the plurality of single volumes can contain the same, or a different, amount and type of contents relative to another single volume; and
    wherein the perforation site is configured to decouple a guidewire attached to the multi-volume balloon by tearing the two adjacent single volumes apart at the perforation site; and
    wherein the guidewire is decoupled with an outer volume of the plurality of single volumes at the perforation site.

2. The multi-volume balloon according to claim 1, wherein the single volumes are compartments of at least two pieces of foil bonded together at the perforation site, wherein the bonding is selected from the group consisting of: ultrasonic welding, thermal welding using a light source, thermal welding using a heat source, pressure welding, swaging, joining, gluing, and stitching.

3. The multi-volume balloon according to claim 1, wherein a material of the plurality of single volumes is selected from the group consisting of: foil, mesh, tube, silicone rubber, elastomeric rubber, polyether ether ketone (or PEEK), polyether ketone ketone (or PEKK), polyethelyene (or PE), polyethelyene terephthalate (or PET), polyurethane (or PU), thermoplastic polyurethane (or TPU), and polycarbonate urethane (or PCU).

4. A multi-volume balloon for treating clinical consequences of degenerative disc disease, vertebral body bone defects, and spinal motion segment instability comprising a plurality of single volumes connected to one another along a perforation site located between two adjacent single volumes that provides a pre-determined breaking point between the single volumes, wherein each single volume is individually adjustable and expandable such that (a) each single volume can contain a variable volume of contents, and (b) each of the plurality of single volumes can contain the same, or a different, amount and type of contents relative to another single volume,     wherein the single volumes are compartments of at least two pieces of foil bonded together at the perforation site, wherein the bonding is selected from the group consisting of: ultrasonic welding, thermal welding using a light source, thermal welding using a heat source, pressure welding, swaging, joining, gluing, and stitching.

\* \* \* \* \*